(12) United States Patent
Parker

(10) Patent No.: US 11,846,495 B2
(45) Date of Patent: Dec. 19, 2023

(54) PROJECTILE WITH TARGET CATEGORIZATION

(71) Applicant: Insights International Holdings, LLC, Franklin, VA (US)

(72) Inventor: Evan Parker, Newsoms, VA (US)

(73) Assignee: INSIGHTS INTERNATIONAL HOLDINGS, LLC, Franklin, VA (US)

( * ) Notice: Subject to any disclaimer, the term of this patent is extended or adjusted under 35 U.S.C. 154(b) by 716 days.

(21) Appl. No.: 17/004,895

(22) Filed: Aug. 27, 2020

(65) Prior Publication Data
US 2021/0063129 A1    Mar. 4, 2021

Related U.S. Application Data

(60) Provisional application No. 62/894,276, filed on Aug. 30, 2019.

(51) Int. Cl.
| | | |
|---|---|---|
| F42B 12/36 | (2006.01) | |
| G01H 1/00 | (2006.01) | |
| H04Q 9/00 | (2006.01) | |
| G10L 25/51 | (2013.01) | |
| A61B 5/11 | (2006.01) | |
| A61B 5/00 | (2006.01) | |
| A61B 7/00 | (2006.01) | |
| F41G 1/00 | (2006.01) | |
| F41J 1/00 | (2006.01) | |

(52) U.S. Cl.
CPC .......... *F42B 12/365* (2013.01); *A61B 5/0002* (2013.01); *A61B 5/1102* (2013.01); *A61B 5/7282* (2013.01); *A61B 5/746* (2013.01); *A61B 7/00* (2013.01); *F41G 1/00* (2013.01); *F41J 1/00* (2013.01); *G01H 1/00* (2013.01); *G10L 25/51* (2013.01); *H04Q 9/00* (2013.01); *A61B 2562/0204* (2013.01); *A61B 2562/0219* (2013.01)

(58) Field of Classification Search
CPC ..................................................... F42B 12/365
See application file for complete search history.

(56) References Cited

U.S. PATENT DOCUMENTS

| | | | | |
|---|---|---|---|---|
| 10,119,798 B2* | 11/2018 | Parker | .......... | F42B 12/365 |
| 2007/0262874 A1* | 11/2007 | Sumrall | .......... | F42B 12/365 |
| | | | | 340/539.13 |
| 2011/0148884 A1* | 6/2011 | Zeleny | .......... | G10H 1/0008 |
| | | | | 84/622 |
| 2013/0257656 A1* | 10/2013 | Parker | .......... | F42B 12/365 |
| | | | | 89/7 |
| 2016/0131464 A1* | 5/2016 | Rubin | .......... | F42B 12/54 |
| | | | | 102/501 |
| 2017/0336185 A1* | 11/2017 | Parker | .......... | F42B 12/365 |
| 2021/0285748 A1* | 9/2021 | Koontz | .......... | F42B 12/365 |

FOREIGN PATENT DOCUMENTS

| | | | | |
|---|---|---|---|---|
| DE | 102016005911 A1 * | 11/2017 | .......... | F42B 12/365 |
| WO | WO-2019132758 A1 * | 7/2019 | .......... | F42B 12/365 |

* cited by examiner

*Primary Examiner* — Bret Hayes
(74) *Attorney, Agent, or Firm* — Fish IP Law, LLP

(57) ABSTRACT

A system for identifying targets wherein a projectile includes one or more sensors that gather sensor data about the environment and send the gathered data to a computing device. The computing device identifies the target by comparing the gathered sensor data to digital sensor signatures known to correspond to different types of objects. The system is also capable of identifying changes in a status of a target based on a change in the sensor data.

14 Claims, 4 Drawing Sheets

PROJECTILE WITH TARGET CATEGORIZATION

This application claims priority to U.S. provisional application 62/894,276, filed Aug. 30, 2019. U.S. provisional application 62/894,276 and all other extrinsic references contained herein are incorporated by reference in their entirety.

FIELD OF THE INVENTION

The field of the invention is ordnance with electronic payloads.

BACKGROUND

The background description includes information that may be useful in understanding the present invention. It is not an admission that any of the information provided herein is prior art or relevant to the presently claimed invention, or that any publication specifically or implicitly referenced is prior art.

Until now, attempts have been made to incorporate sensors and other types of packages into ordnance such as bullets, especially small arms munitions, to obtain information about the targets. However, existing solutions are limited in terms of the information they can provide the shooter or other operator as they are limited to location or position tracking. Attempts to provide additional information involve complicated systems and sensors, which are costly, prone to failure, and fail to accommodate smaller-caliber munitions.

Thus, there is a need for a bullet system that can provide additional information to the shooter in a reliable fashion without the need to introduce overly complicated systems into ordnance.

SUMMARY OF THE INVENTION

The inventive subject matter provides apparatus, systems and methods in which a target/object into which a projectile has been embedded can be properly identified.

The system includes a projectile that has a sensor capable of detecting movement, sound and/or vibration and a communication interface that relays the detected movement and/or vibration in the form of sensor data to a computing device.

The computing device of the inventive subject matter receives the sensor data and identifies a digital sensor signature that corresponds to the object based on the received sensor data. The computing device can then provide information about the object to an operator based on the digital sensor signature.

To identify the object in which the projectile has been embedded, the computing device compares the received sensor data against available digital sensor signatures to find a match. The object associated with the matching digital sensor signature is then correctly identified as the target/object in which the projectile is embedded.

In embodiments, the digital sensor signature is a biosignal signature, reflecting a biosignal of a biological organism. In a variation of these embodiments, the biosignal signature is a heartbeat signature corresponding to the heartbeat of the respective biological organism.

In embodiments, the computing device can determine a status change in the target based on a change in the received sensor data that exceeds a threshold for change. The computing device can then notify the user of a status change. For example, in embodiments, the change in the received sensor data can be an interruption in the data stream or signal pattern that would reflect the death of a biological organism.

Various objects, features, aspects and advantages of the inventive subject matter will become more apparent from the following detailed description of preferred embodiments, along with the accompanying drawing figures in which like numerals represent like components.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

The following description includes information that may be useful in understanding the present invention. It is not an admission that any of the information provided herein is prior art or relevant to the presently claimed invention, or that any publication specifically or implicitly referenced is prior art.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

DETAILED DESCRIPTION

Throughout the following discussion, numerous references will be made regarding servers, services, interfaces, engines, modules, clients, peers, portals, platforms, or other systems formed from computing devices. It should be appreciated that the use of such terms, is deemed to represent one or more computing devices having at least one processor (e.g., ASIC, FPGA, DSP, x86, ARM, ColdFire, GPU, multi-core processors, etc.) programmed to execute software instructions stored on a computer readable tangible, non-transitory medium (e.g., hard drive, solid state drive, RAM, flash, ROM, etc.). For example, a server can include one or more computers operating as a web server, database server, or other type of computer server in a manner to fulfill described roles, responsibilities, or functions. One should further appreciate the disclosed computer-based algorithms, processes, methods, or other types of instruction sets can be embodied as a computer program product comprising a non-transitory, tangible computer readable media storing the instructions that cause a processor to execute the disclosed steps. The various servers, systems, databases, or interfaces can exchange data using standardized protocols or algorithms, possibly based on HTTP, HTTPS, AES, public-private key exchanges, web service APIs, known financial transaction protocols, or other electronic information exchanging methods. Data exchanges can be conducted over a packet-switched network, the Internet, LAN, WAN, VPN, or other type of packet switched network.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

The following description includes information that may be useful in understanding the present invention. It is not an admission that any of the information provided herein is prior art or relevant to the presently claimed invention, or that any publication specifically or implicitly referenced is prior art.

Figure 1:
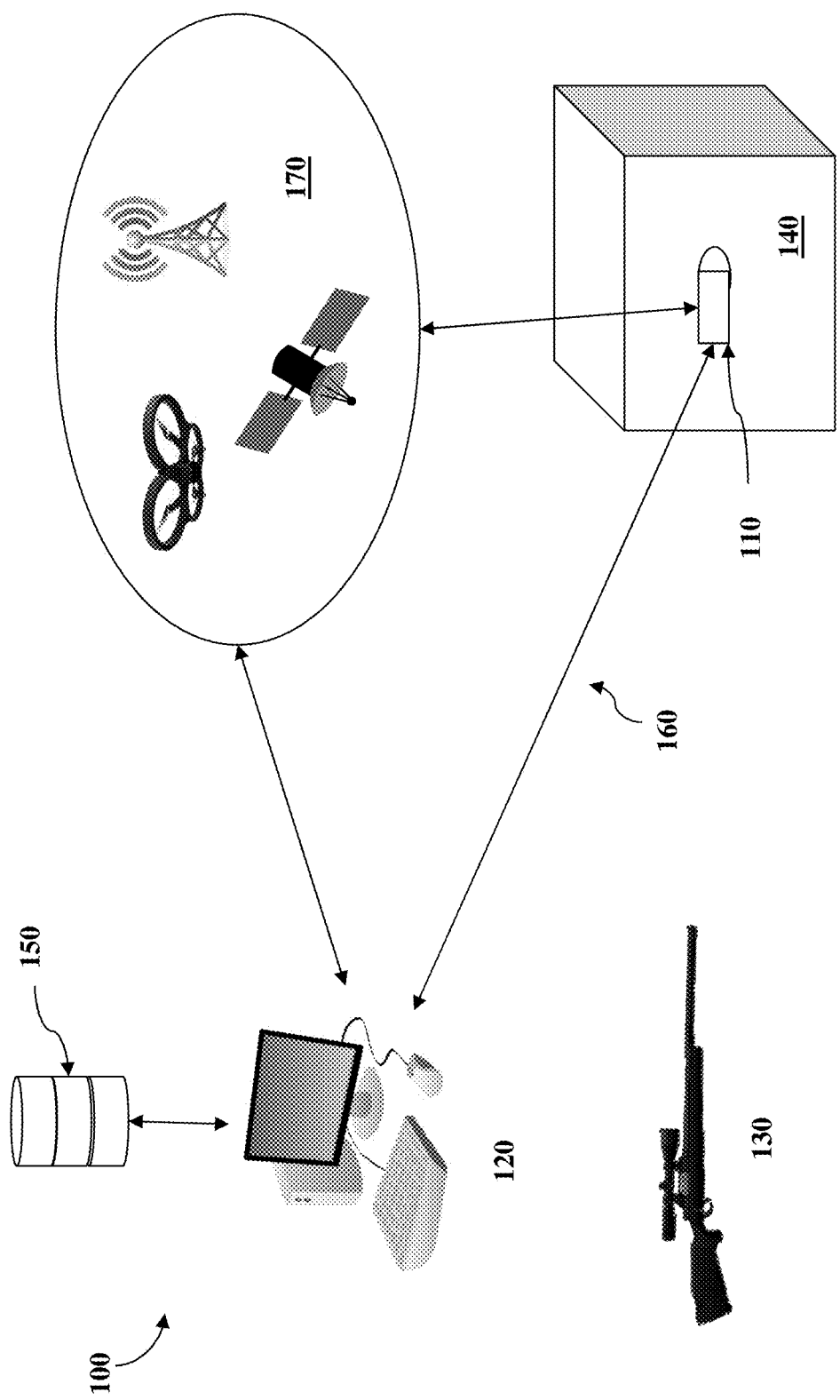
FIG. 1 is a diagrammatic overview of the various components of the system according to an embodiment of the inventive subject matter.

FIG. 1 provides a diagrammatic overview of a system 100 according to an embodiment of the inventive subject matter. FIG. 1 shows ordnance 110 (in this example, a bullet) having been fired by weapon 130 (in this case, a rifle) and struck a target 140, within which it is embedded. The ordnance 110 can be lethal ordnance or non-lethal ordnance. At some point prior to or during the bullet 110 becoming embedded within target 140 (such as when fired from the discharging weapon, upon impact with the target 140, or at a different point in time), the electronics components carried within the bullet 110 activate and the bullet 110 can communicate information back to computing device 120, including the information about the target as discussed in further detail below.

It should be noted that while the discussion herein refers to the weapon 130 as "rifle 130", it is for the purposes of discussion only. Any other suitable weapon is contemplated to be used with the systems and methods of the inventive subject matter.

Depending on the type of wireless communications equipment carried by the bullet 110, the distance between the bullet 110 and the computing device 120 and other factors such as line-of-sight, obstructions, weather conditions, etc., the bullet 110 and the computing device 120 can communicate either directly as shown by the arrows 160 or indirectly via a relay 170 (e.g., a drone, a cellular tower, a satellite, a Wi-Fi router, another computing device, etc.).

Any suitable system or method for deploying an electronics package into a target can be used with the systems and methods of the inventive subject matter. It should be noted that in FIG. 1, the bullet 110 is shown embedded within target 140 for the sake of simplicity of illustration. Certain suitable methods and systems for deploying ordnance-based electronics payloads within targets, such as those described in Applicant's commonly-owned provisional application 62/860,639 entitled "Ordnance Ballistics Deployment System", do not necessarily result in the entirety of the bullet remaining within the target as certain sections may not enter the target and/or may exit out the other side of the target. For the purposes of this discussion, references to the bullet 110 embedded within a target (such as target 140) are intended to refer to the successful deployment of an electronics payload within a target without requiring the entirety bullet to be so embedded.

In the example of FIG. 1, the rifle 130 representing the shooter and the computing device 120 are illustrated as being separate. However, it is contemplated that the same person could be the shooter of the rifle 130 and the operator of computing device 120. It is also contemplated that the shooter and the operator of the computing device 120 could be different people, such as a shooter and a spotter or partner in a military unit. Alternatively/additionally, the operator of computing device 120 may be in an entirely different location than the shooter of rifle 130, such as at a remote headquarters.

The computing device 120 includes at least one processor, at least one non-transitory computer-readable storage medium, at least one communication interface enabling data exchange, and at least one user output interface that allows for the output of information (e.g., a screen, audio output, tactile feedback, heads-up display, etc.). The computing device 120 can also include a user input interface allowing for user interaction with the computing device 120 (e.g., a touch screen, stylus, mouse, keyboard, joystick, etc.). Examples of computing device 120 include, but are not limited to, a desktop computer, a laptop computer, a tablet, and a cellular phone.

In embodiments, it is contemplated that the computing device 120 can be integrated in whole or in part to wearable equipment that is worn by the soldier. For example, some or all of the computing device 120 can be helmet-mounted such that the soldier is able to view the presented information via a heads-up display on a visor or headset, and enter commands via a microphone, a keypad worn on their wrist, or some other input interface.

It is contemplated that, in embodiments, the computing device 120 can be partially or entirely mounted on, integrated with, or otherwise on board the rifle 130 to provide a soldier with a complete, compact system. For example, one or more of an antenna, processing components, display, etc. can be integrated or mounted on the weapon.

As seen in FIG. 1, the computing device 120 is communicatively coupled with a database 150. The database 150 includes one or more non-transitory computer-readable storage media (e.g., hard drives, solid state drives, RAM, ROM, etc.) that store a plurality of digital sensor signatures corresponding to a plurality of objects.

Figure 2:
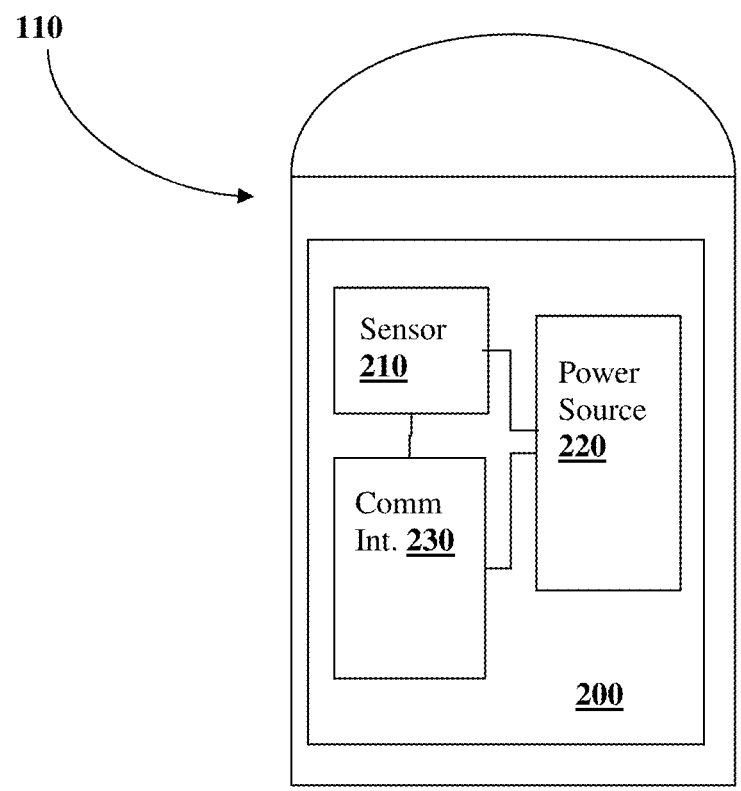
FIG. 2 provides a diagrammatic view of the bullet of the inventive subject matter in greater detail.

FIG. 2 illustrates bullet 110 of FIG. 1 in greater detail. As seen in FIG. 2, bullet 110 includes an electronics payload 200 that contains at least one sensor 210, a power source 220 (e.g., a battery), and a communications interface 230.

In the embodiment shown in FIGS. 1-2, the sensor 210 is an accelerometer that detects acceleration forces experienced by the bullet 110 while embedded within target 140. It is contemplated that the accelerometer used in the systems and methods of the inventive subject matter is a sufficiently sensitive accelerometer such that it not only detects movement of the bullet 110 but also vibrations experienced by the bullet 110 (such as vibrations caused by target 140).

As discussed herein, in preferred embodiments of the inventive subject matter, the sensor 210 comprises an accelerometer. However, other sensors capable of detecting vibrations are contemplated. For example, in other embodiments, the sensor 210 can comprise a microphone, which can detect vibrations in the form of sound.

In embodiments, the bullet 110 can include additional sensors instead of or in addition to the vibration sensors discussed above. Other suitable sensors can include temperature sensors, light sensors, moisture sensors, pressure sensors, sound sensors and electrical sensors (e.g., voltage or current, magnetic fields).

As mentioned above, it is contemplated that the bullet 110 can include more than one sensor 210 in embodiments. In these embodiments, the sensors 210 are collectively capable of detecting characteristics about the environment in multiple modalities. For example, the sensors 210 can include an accelerometer and a temperature sensor that are collectively capable of gathering movement/vibration information and temperature information about the bullet's environment.

In embodiments, the one of the sensors in the bullet 110 can be a network sensor capable of detecting the presence of a wireless network (e.g., a Bluetooth network, Wifi network, cellular network, etc.). The network sensor can be a network radio capable of accessing the available network, such as to monitor traffic, upload a virus, etc.

In embodiments, the bullet 110 can also include one or more of a positioning component (e.g., GPS component) for location tracking, a processor for onboard processing capabilities, and/or a non-transitory physical memory to store instructions for execution by an on-board processing. In embodiments where the bullet 110 includes a processor, some or all of the functions discussed with regard to the computing device 120 can be performed by the processor of the bullet 110 and the results of those functions communicated to the computing device 120 for subsequent processing and/or presentation to the operator.

Figure 3:
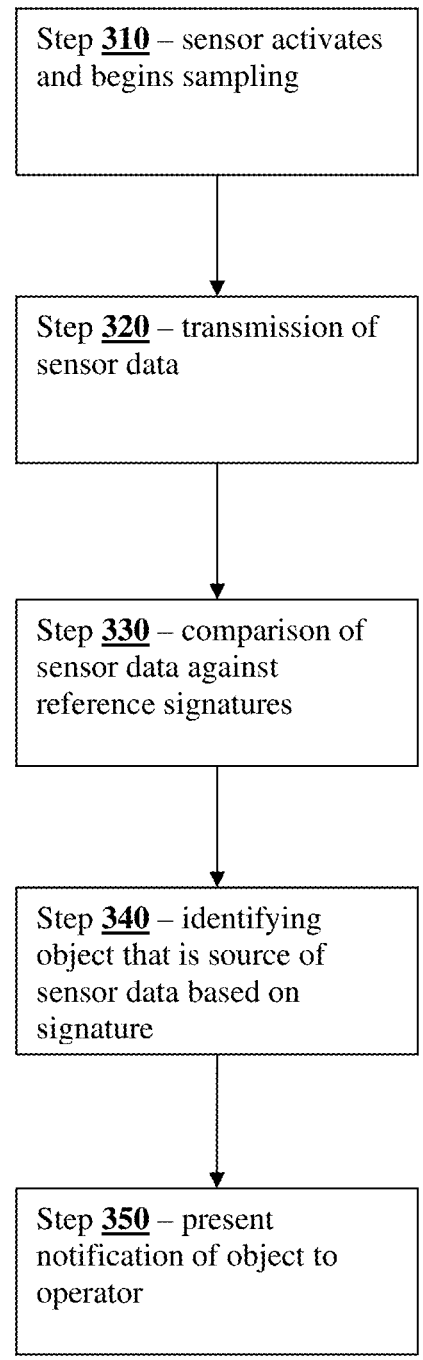
FIG. 3 is a flowchart of the processes executed by the various system components of the inventive subject matter.

FIG. 3 illustrates a flowchart of the processes executed by the various system components of the inventive subject matter.

At step 310, the sensor 210 is activated and begins sampling to detect any acceleration as discussed above. Upon activation, the sensor 210 is continuously sampling and as such detects acceleration experienced by the bullet 110, such as due to movement, vibrations, etc.

Various suitable methods of activating electronic components within ordnance are contemplated for activating the electronics components of bullet 110 and will not be discussed further here. Examples of suitable methods include, but are not limited to, the methods discussed in Applicant's commonly-owned provisional application 62/860,639 entitled "Ordnance Ballistics Deployment System" and Applicant's commonly-owned U.S. patent application Ser. No. 16/439,413 entitled "Electronically Tracked Synthetic Ordnance."

At step 320, the sensor data corresponding to the sampling by sensor 210 is transmitted via communications interface 230 to computing device 120. The sampling is transmitted in the form of sensor data via the communications interface 230 to the computing device 120 operated by the shooter or other operator. If the sensor 210 has sensed any acceleration forces, the sensor data will include data corresponding to the detected acceleration.

At step 330, the computing device 120 receives the sensor data and compares it against the digital sensor signatures stored in database 150. The patterns in the received sensor data are compared against the known patterns of the digital sensor signatures for various objects.

The digital sensor signatures are sensor patterns in the same modality of sensor 210, established a priori through the sampling of sensors embedded within known objects in various environments.

By sampling the sensor readings of sensors installed within various known objects, the database is populated with the digital sensor signatures corresponding to various objects and various environments. For example, a vibration sensor within a human being could detect sensor data that could include heartbeats and other vibration signals typically produced by the human body (for example, as a "human vibration signature"). The sensor data pattern of the heartbeat and other vibration signals can then be stored as a digital sensor signature.

In embodiments, the sensor 210 is sufficiently sensitive such that the sensor data is of a sufficient fidelity to allow the system is able to identify different objects of a same object type. For example, in these embodiments, the system is capable of distinguishing between different types of engines (e.g., diesel versus gasoline), distinguish between different types of vehicles (e.g., aircraft versus automobile), the biosignals of different types of animals, etc., by being able to identify particular sensor signatures as discussed herein.

The types of sensor signatures contemplated in the inventive subject matter includes, but is not limited to, biological sensor signatures (e.g., human sensor signatures, animal sensor signatures for different types of animals), vehicle/engine sensor signatures (e.g., vehicle engines and other sensor readings particular to vehicles of various types), and electronic sensor signatures (e.g., wireless communication emissions, magnetic equipment emissions, etc.).

At step 340, upon finding a match, the computing device 120 identifies the object as the object associated with the digital sensor signature that matched with the received sensor data.

Continuing with the example above, As such, when vibration sensor data is received from an embedded bullet, it is compared to the stored human vibration signature and if there is a match, then the type of target (i.e., a human being) has been positively identified.

At step 350, the computing device 120 presents a notification of the identified object to the operator of the computing device 120.

In embodiments, the system can report a "miss" to the operator. If the computing device 120 is not able to match the received sensor data to any stored digital sensor signatures, the computing device 120 reports a "miss" to the operator because the lack of identifiable signal sensor data is reflective of the bullet not ending up in a known target and as such not in a target of interest. For example, if the bullet hits an object in the environment such as the ground, a tree, etc. that does not have a detectable movement or vibration and a corresponding digital sensor signature, the system reports a "miss" to the operator.

In other embodiments, the system can report a status of "unknown" to the operator if the sensor does not pick up a recognizable pattern. For example, if the bullet hits an object in the environment such as the ground, a tree, etc. that does not have a detectable movement or vibration and a corresponding digital sensor signature, the system reports a status of "unknown" to the operator.

In embodiments, the systems and methods of the inventive subject matter can detect a change in the status or condition of the impacted target and communicate this change to an operator. For example, if the target 140 is a live object (e.g., an animal or human), the system 100 is capable of determining status changes such as increased stress or when the live object dies and communicate that change in status to the operator accordingly. The process executed by the system is as follows:

After impacting the live target, the target is identified according to the process of FIG. 3. For live objects, applicable digital sensor signatures can include biosignals such as heartbeat patterns corresponding to human beings or other animals, to properly identify the type of live object impacted by the bullet.

Figure 4:
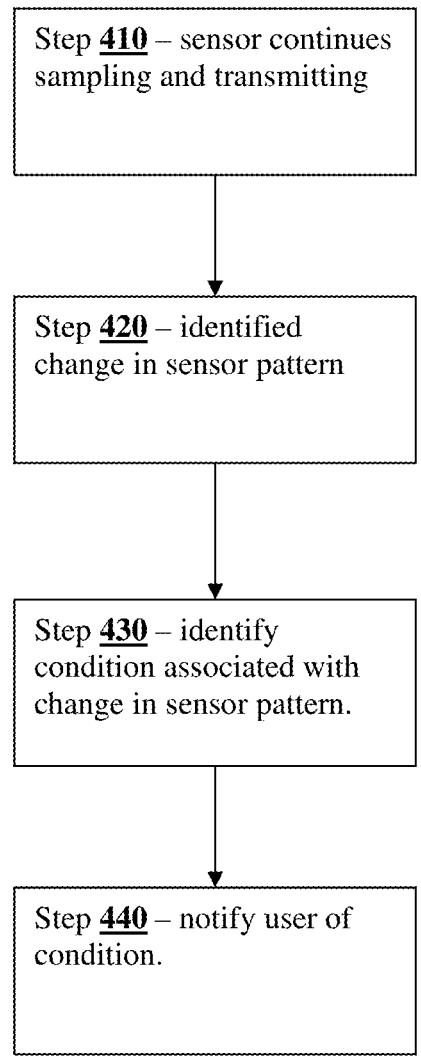
FIG. 4 provides a flow chart of a change in status of a target, according to embodiments of the inventive subject matter.

FIG. 4 provides a flow chart according to these embodiments of the inventive subject matter.

Following the identification of a live object at step 340 and/or the notification at step 350, the sensor 210 continues to sample its environment (the impacted target) and transmit the sensor data to the computing device 120 at step 410.

The computing device 120, having identified the object, continues to analyze the received sensor pattern for any changes in the pattern. Examples of changes can include a change in the pattern frequency, a change in the pattern intensity, or an interruption or cessation of the pattern.

At step 420, the computing device 120 identifies a change in the sensor pattern. For example, the detection can include detecting a variation in frequency, speed, intensity or other sensor metric beyond a pre-determined threshold of variation.

In these embodiments, the digital sensor signatures stored in database 150 include threshold parameters and, for each of the various threshold parameters, a corresponding identification of a condition associated with the detection of the parameters being exceeded. As step 430, the computing device 120 retrieves the corresponding identification of the condition and provides the notification to the user at step 440.

For example, an interruption in the sensor pattern can be associated with the condition of the identified object dying (wherein the interruption of the pattern corresponds to a stop in a heartbeat or pulse). Thus, if the computing device 120 detects that sensor pattern is interrupted for a pre-determined amount of time, the computing device 120 is programmed to present the corresponding condition associated with this interruption to the user, notifying the user that the object has deceased.

In another example, the sensor pattern associated with an engine may cease indicating that the engine has been turned off. This change would be detected by the computing device 120, which would report this accordingly. If the engine is turned on, the sensor 210 would once again detect the engine and the computing device 120 would determine, based on the resumed sensor data, that the engine has been turned on again. It could then give a notification to the user that the engine has been reignited, possibly indicating that the target will once again be on the move.

In embodiments of the inventive subject matter, the system is capable of detecting more than one object based on the received sensor data because the received sensor data may include multiple sensor patterns. For example, the system can detect that the target the bullet is embedded is a person and also that the person is riding in a car.

In these embodiments, the computing device 120 finds more than one match at step 340 and/or identified additional matches after finding a first match at step 340. Because the sensor data in these embodiments is assumed to carry more than one pattern, the computing device 120 will identify each of the patterns by matching them against the plurality of digital sensor signature patterns stored in the database. The computing device 120 can then notify the user of both objects and their status.

Typically, the detected signal corresponding to the object in which the bullet 110 is embedded will be of a greater magnitude than objects in the environment. As such, the computing device 120 can compare the intensity or magnitude of the detected signal patterns in the received sensor data and report the object associated with the signal pattern having greater magnitude as a primary object (i.e., the object in which the bullet is embedded) and any object(s) associated with signal pattern(s) of lesser magnitude as secondary objects (i.e., objects in the environment or objects surrounding the first object).

For example, if a signal pattern corresponding to heartbeat has a larger magnitude than a second signal pattern that is correlated with a vehicle engine, the computing device 120 determines that the bullet 110 is embedded in a human that is in the vicinity of a vehicle (i.e., riding in a vehicle) and reports accordingly to the operator.

In embodiments, the computing device 120 is programmed to filter out signal noise that does not correspond to identified patterns.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A system for target identification, comprising:
   a projectile comprising:
      a sensor configured to detect at least one of movement, sound or vibration as sensor data; and
      a first communication interface communicatively coupled to the sensor, configured to transmit the sensor data; and
   a computing device comprising at least one processor and a second communication interface, the computing device programmed to:
      receive, via the second communication interface, the sensor data gathered by the sensor;
      identify a digital sensor signature corresponding to a physical object based on the received sensor data; and
      provide a notification regarding the physical object to a user based on the identified digital sensor signature.

2. The system of claim 1, wherein the digital sensor signature corresponding to the physical object comprises at least one of a vibration pattern or a sound pattern associated with the physical object.

3. The system of claim 2, wherein the sensor data comprises at least one of vibration data or sound data captured by the sensor.

4. The system of claim 3, wherein identifying the digital sensor signature further comprises matching the at least one of captured vibration data or captured sound data against the respective at least one of the vibration pattern or sound pattern.

5. The system of claim 1, wherein the physical object comprises a biological organism and the digital sensor signature comprises a biosignal signature.

6. The system of claim 5, wherein the biosignal signature comprises a heartbeat signature.

7. The system of claim 6, wherein the computing device is programmed to:
   detect a change in a characteristic of the received sensor data;
   determine that the change exceeds a threshold;
   correlate the change to a status change regarding the biological organism; and
   provide a notification regarding the status change to the user.

8. The system of claim 7, further comprising wherein:
   the sensor data comprises a signal pattern;
   the change in the characteristic comprises an interruption of the signal pattern; and
   the status change correlated to the interruption of the signal pattern comprises a death of the biological organism.

9. The system of claim 1, wherein the physical object comprises a vehicle and the object signature comprises an engine signature.

10. The system of claim 1, wherein the computing device is further programmed to:
   identify a second digital sensor signature corresponding to a second physical object based on the received sensor data; and provide a notification regarding the second physical object to the user based on the identified second digital sensor signature.

11. The system of claim 1, further comprising a database storing a plurality of digital sensor signatures corresponding to a respective plurality of physical objects.

12. The system of claim 1, wherein the sensor data comprises movement and the sensor comprises an accelerometer.

13. The system of claim 1, wherein the sensor data comprises sound and the sensor comprises a microphone.

14. The system of claim 1, wherein the computing device is further programmed to, in response to a failure to identify a digital sensor signature corresponding to a physical object based on the received sensor data, provide a notification reporting a miss to the user.

* * * * *